(12) United States Patent
Mueller et al.

(10) Patent No.: US 8,084,658 B2
(45) Date of Patent: Dec. 27, 2011

(54) INTEGRATED PROCESS FOR PREPARING BENZENE AND AMMONIA FROM ALIPHATIC HYDROCARBONS AND NITROGEN

(75) Inventors: Ulrich Mueller, Neustadt (DE); Harald Freiberger, Dannstadt-Schauernheim (DE)

(73) Assignee: BASF SE, Ludwigshafen (DE)

( * ) Notice: Subject to any disclaimer, the term of this patent is extended or adjusted under 35 U.S.C. 154(b) by 362 days.

(21) Appl. No.: 12/516,083

(22) PCT Filed: Nov. 22, 2007

(86) PCT No.: PCT/EP2007/062668
§ 371 (c)(1),
(2), (4) Date: May 22, 2009

(87) PCT Pub. No.: WO2008/062028
PCT Pub. Date: May 29, 2008

(65) Prior Publication Data
US 2010/0056836 A1     Mar. 4, 2010

(30) Foreign Application Priority Data
Nov. 24, 2006 (EP) .................................. 06124710

(51) Int. Cl.
*C07C 2/76* (2006.01)
*C01B 21/087* (2006.01)

(52) U.S. Cl. ........ 585/322; 585/418; 585/419; 585/420; 423/359

(58) Field of Classification Search .................. 585/322, 585/418, 419, 420; 423/359
See application file for complete search history.

(56) References Cited

U.S. PATENT DOCUMENTS

| | | | |
|---|---|---|---|
| 4,689,208 A | 8/1987 | Pinto | |
| 4,727,206 A | 2/1988 | Clayson et al. | |
| 5,032,364 A | 7/1991 | Pinto | |
| 2002/0072642 A1 | 6/2002 | Allison et al. | |

FOREIGN PATENT DOCUMENTS

JP    2 267116    10/1990

OTHER PUBLICATIONS

Liu, C.-J., "Comparative Investigations on Plasma Catalytic Methane Conversion to Higher Hydrocarbons Over Zeolites", Applied Catalysis A: General, vol. 178, No. 1, pp. 17-27 (1999).
Liu, H. et al., "Methane Dehydroaromatization Over Mo/HZSM-5 Catalysts: The Reactivity of MoCx Species Formed From MoOx Associated and Non-Associated With Broensted Acid Sites", Applied Catalysis A: General, vol. 295, pp. 79-88 (2005).
Hassan, A., "Highly Active, Selective and Stable Mo/Ru/HZSM-5 Catalysts for Oxygen-Free Methane Aromatization", Applied Catalysis A: General, vol. 297, pp. 159-164 (2006).
Wang, L. et al., "Dehydrogenation and Aromatization of Methane Under Non-Oxidizing Conditions", Catalysis Letters, vol. 21, pp. 35-41 (1993).
Wellenbuescher, J. et al., "The Application of Ru-Exchanged Zeolite NaY in Ammonia Synthesis", Studies in Surface Science and Catalysis, vol. 84, pp. 941-948 (1994).
U.S. Appl. No. 12/601,022, filed Nov. 20, 2009, Schubert, et al.
U.S. Appl. No. 13/003,839, filed Jan. 12, 2011, Schubert, et al.

*Primary Examiner* — Thuan Dinh Dang
(74) *Attorney, Agent, or Firm* — Oblon, Spivak, McClelland, Maier & Neustadt, L.L.P.

(57) ABSTRACT

Process for the integrated preparation of aromatics and ammonia by reaction of a gas stream A comprising at least one $C_1$-$C_6$-aliphatic and nitrogen in the presence of at least one catalyst, wherein the $C_1$-$C_6$-aliphatics are converted non-oxidatively into aromatics in one reaction and the hydrogen liberated in this reaction is reacted with nitrogen to form ammonia in a further reaction.

12 Claims, No Drawings

INTEGRATED PROCESS FOR PREPARING BENZENE AND AMMONIA FROM ALIPHATIC HYDROCARBONS AND NITROGEN

The present invention relates to a process for the integrated preparation of aromatics and ammonia from a gas stream comprising $C_1$-$C_6$-aliphatics and $N_2$.

Aromatic hydrocarbons such as benzene, toluene and naphthalene are important intermediates in the chemical industry for which the demand continues to increase. They are generally obtained by catalytic reforming of naphtha which is in turn obtained from petroleum. Recent studies have shown that worldwide petroleum reserves will become exhausted more quickly than natural gas reserves. The preparation of benzene from natural gas an alternative raw material is therefore an interesting alternative to conventional processes. The main component of natural gas is methane.

The nonoxidative conversion of methane into benzene and hydrogen in the presence of Mo- or Zn-comprising HZSM-5 zeolite catalysts, sometimes with formation of by-products such as ethylene, naphthalene and further, higher hydrocarbons, has been known for a relatively long time (Wang et al., Catalysis Letters 21, 35-41 (1993)) and is also referred to as dehydrogenative aromatization. In this context, nonoxidative means that the reaction is carried out in the absence of an oxidant, in particular in the absence of oxygen.

Liu et al., Applied Catalysis A: General 295, 79-88 (2005), report selectivities of from about 60% to 80% for the nonoxidative conversion of methane into benzene and naphthalene over Mo-doped HZSM-5 zeolites, depending on the Mo content of the catalyst.

Hassan et al., Applied Catalysis A: General 297, 159-164 (2006), obtained methane conversions of up to 6.4% at selectivities to benzene of from 62 to 84% in the nonoxidative conversion of methane into aromatics over ZSM-5 zeolites doped with Ru and Mo, with significantly increased operating lives of the catalyst and at low temperatures.

The nonoxidative aromatization of methane and higher alkanes is limited by the position of the thermodynamic equilibrium. In the nonoxidative aromatization of methane, 9 molecules of $H_2$ are liberated for each molecule of benzene formed, so that this reaction can also be utilized for obtaining pure $H_2$ which is used, for example, in fuel cells. The separation of the hydrogen formed from unreacted methane and higher alkanes and also from aromatics formed in the aromatization reaction is generally difficult and can be carried out only with a high outlay in terms of apparatus. It can be achieved, for example, by means of a hydrogen-permeable membrane or by means of adsorption processes. The hydrogen separated off can subsequently be used further.

Due to the position of the thermodynamic equilibrium, the alkane conversions in the nonoxidative aromatization are low and, even at high selectivities of the reaction, lead to comparatively low yields of aromatics. The gas stream obtained after separation of the aromatics from the product gas stream can be recirculated to the aromatization reaction in order to increase the yields based on alkanes used, but also comprises the hydrogen formed in the aromatization, which has an unfavorable effect on the position of the thermodynamic equilibrium. To avoid the unfavorable influence of the hydrogen, the hydrogen would have to be removed from the gas stream before the latter is recirculated. As indicated above, this is possible only with the aid of a comparatively high outlay in terms of apparatus.

Ammonia is a further important intermediate in the chemical industry. One source of ammonia would be the gas water from coke-producing plants and gas-producing facilities. However, the synthesis of ammonia by the Haber-Bosch process is substantially more important. This process has been known for a long time and about 90% of the world production of $NH_3$ are nowadays produced by it. The hydrogen required for the synthesis is usually prepared by reaction of steam with coke or hydrocarbons and has to be freed of the carbon oxides formed in the process in further steps.

A further method of synthesizing ammonia is described by Wellenbücher et al. in Zeolites and Related Microporous Materials: State of the Art 1994, Studies in Surface Science and Catalysis, Vol. 84 (1994, 941-948), Elsevier Science. Nitrogen conversions close to the thermodynamic equilibrium are achieved in the reaction of a mixture of $N_2$ and $H_2$ in a ratio of 1:3 over zeolites of the NaY type comprising 5% by weight of Ru at temperatures of 843 K.

It is an object of the present invention to provide a process for preparing aromatics from $C_1$-$C_6$-aliphatics, which leads to high yields of aromatics and in which the complicated removal of hydrogen is very largely dispensed with and the by-products formed in the aromatization reaction can be utilized economically.

This object is achieved according to the invention by a process for the integrated preparation of aromatics and ammonia by reaction of a gas stream A comprising at least one $C_1$-$C_6$-aliphatic and nitrogen in the presence of at least one catalyst, preferably a zeolite catalyst, wherein the $C_1$-$C_6$-aliphatics are converted nonoxidatively into aromatics in one reaction and the hydrogen liberated in this reaction is reacted with nitrogen to form ammonia in a further reaction.

The hydrogen which is liberated in stochiometric amounts in the nonoxidative aromatization is here converted without a separation step into a further economically useful product.

An advantage of the process of the invention is the simultaneous production of two important basic products of industrial chemistry. The ammonia prepared in addition to the aromatics has the additional advantage that, owing to its boiling point and its very good solubility in water, it can easily be separated off from the product stream. Furthermore, the formation of ammonia withdraws $H_2$ from the reaction mixture, so that the equilibrium of the aromatization reaction should be shifted to the side of the aromatics. A further advantage of the process of the invention is the combination of an endothermic reaction (nonoxidative dehydrogenative aromatization) with an exothermic reaction (formation of ammonia from $N_2$ and $H_2$), so that the energy balance of the process of the invention is significantly more favorable than that of a pure, nonoxidative dehydroaromatization.

An advantage with regard to the synthesis of ammonia is the in-situ provision of the hydrogen necessary for this, which otherwise has to be prepared in a process preceding the ammonia synthesis. In addition, some purification steps which are otherwise necessary, in which by-products which are formed in the preparation of hydrogen and are undesirable or harmful for the further use are separated off, are dispensed with, as, for example, comparison with the Haber-Bosch process shows.

According to the invention, the gas stream A comprises at least one aliphatic having from 1 to 6 carbon atoms. It is possible to use, for example, methane, ethane, propane, n-butane, isobutene, n-pentane, isopentane, n-hexane, isohexane and 2,3-dimethylbutane and also mixtures thereof. Preference is given to using aliphatics having from 1 to 4 carbon atoms, i.e. methane, ethane, propane, n-butane and i-butane.

Natural gas is preferably used as source of the $C_1$-$C_6$-aliphatics. The typical composition of natural gas is as follows: from 75 to 99 mol % of methane, from 0.01 to 15 mol % of ethane, from 0.01 to 10 mol % of propane, up to 6 mol % of butane and higher hydrocarbons, up to 30 mol % of carbon dioxide, up to 30 mol % of hydrogen sulfide, up to 15 mol % of nitrogen and up to 5 mol % of helium. The natural gas can be purified and enriched by methods known to those skilled in the art before being used in the process of the invention. Purification includes, for example, the removal of any hydrogen sulfide or carbon dioxide and further compounds which are undesirable in the subsequent process present in the natural gas.

The natural gas can also be pretreated by the process described in EP 1674555 A by the applicant. In this process, enrichment of methane by passage of the natural gas over MOFs "metal organic frameworks" and reversible adsorption of the undesirable constituents such as carbon dioxide or higher alkanes, with the higher alkanes ethane, propane, n-butane and i-butane being able to be removed selectively, i.e. individually, or together. Both the methane-enriched gas which has been pretreated by this process and the higher hydrocarbons such as ethane, propane, n-butane and i-butane which have been separated off the pretreatment can be used in the process of the invention.

In a further embodiment of the present invention, the higher hydrocarbons having at least two carbon atoms absorbed on the MOFs by the above-described process can be used in the process of the invention after desorption.

Particular preference is given to using natural gas which has a high joule value and has a high proportion of hydrocarbons having more than one carbon atom, known as H gas. These hydrocarbons having more than one carbon atom are ethane, propane, n-butane and i-butane.

The impurities which may be present in the natural gas can also be comprised in gas stream A.

The $C_1$-$C_6$-aliphatics comprised in the gas stream A can also come from other sources. They can have been obtained, for example, in oil refining. The $C_1$-$C_6$-aliphatics can also have been obtained regeneratively (e.g. biogas) or have been prepared synthetically, for example by the Fischer-Tropsch synthesis.

If biogas is used as source of the $C_1$-$C_6$-aliphatics, the gas stream A can additionally comprise ammonia, traces of lower alcohols and further constituents typical of biogas.

The gas stream A comprises $N_2$ which can, for example, be obtained by fractional distillation of liquefied air. The gas stream A can therefore also comprise traces of noble gases such as He, Ne or Ar.

In general, the gas stream A can comprise all impurities and constituents which are already present in the starting materials $C_1$-$C_6$-aliphatics and $N_2$.

The volume ratio of $C_1$-$C_6$-aliphatic to $N_2$ in the gas stream A is in the range from 1:1 to 20:1, preferably from 2:1 to 15:1, particularly preferably from 3:1 to 10:1.

The reaction of the $C_1$-$C_6$-aliphatics and the $N_2$ takes place under nonoxidative conditions, i.e. very largely in the absence of an oxidant, in particular very largely in the absence of oxygen. No water or virtually no water and likewise no or virtually no CO or $CO_2$ are formed from the hydrogen formed in the aromatization and the $C_1$-$C_6$-aliphatics used, respectively.

According to the invention, the reaction of the gas stream A takes place over at least one catalyst, preferably at least one zeolite-based catalyst.

For example, it is possible to use zeolites of the following X-ray-crystallographic structure types: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, SCO, CFI, SGF, CGS, CHA, CHI, CLO, CON, CZP, DAC, DDR, DFO, DFT, DOH, DON, EAB, EDI, EMT, EON, EPI, ERI, ESV, ETR, EUO, FAU, FER, GIS, GIU, GME, GON, GOO, HEU, IFR, IHW, ISV, ITE, ITH, ITW, IWR, IWW, JBW; KFI, LAU, LEV, LIO, LIT, LOS, LOV, LTA, LTL, LTN, MAR, MAZ, MEI, MEL, MEP, MER, MFI, MFS, MON, MOR, MOZ, MSO, MTF, MTN, MTT, MTW, MWW, NAB, NAT, NES, NON, NPO, NSI, OBW, OFF, OSI, OSO, OWE, PAR, PAU, PHI, PON, RHO, RON, RSN, RTE, RTH, RUT, RWR, RWY, SAO, SAS, SAT, SAV, SBE, SBS, SBT, SFE, SFF, SFG, SFH, SFN, SFO, SGT, SOD, SOS, SSY, STF, STI, STT, TER, THO, TON, TSC, UEI, UFI, UOZ, USI, UTL, VET, VFI, VNI, VSV, WIE, WEN, YUG, ZON or mixed structures of two or more of these types. Preference is given to using zeolites of the CHA type, the MFI type, the pentasil type or the FAU type, in particular ZSM zeolites such as ZSM-5, ZSM-8, ZSM-11, ZSM-23 and ZSM-35, preferably ZSM-5, or MCM zeolites such as MCM-22.

The zeolites can comprise further elements of main group 3, e.g. Ga, B or In, in addition to Al. In such a case, preference is given to Ga-comprising zeolites which can be present as framework or extra-framework. As counterions for the excess negative charge produced by the trivalent framework of cations, it is possible for $H^+$, $Na^+$, $Li^+$, $K^+$, $Rb^+$, $Cs^+$, $NH_4^+$, $Mg^{2+}$, $Ca^{2+}$, $Sr^{2+}$ and $Ba^+$ to be comprised in the zeolite.

The zeolites can comprise further elements of main group or transition group 4 e.g. Ti, Ge or Sn, in addition to Si.

The zeolites can be doped with one or more further transition metals. Among these, preference is given to using Mn, Mo, Pd, Pt, Ru, Cu, Co, Fe, Re, W or Zn; particular preference is given to using zeolites doped with Ga, Zn, In, Mo, W, Ru or Pt.

The metals used for doping the catalyst can be applied to the zeolite by the methods known to those skilled in the art. Before application of the metals, the zeolite can, if appropriate, be converted into the H form. This can be achieved, for example, by ion exchange with aqueous $NH_4NO_3$ solution, subsequent drying and, if appropriate, subsequent calcination.

The metals can be applied wet chemically in the form of aqueous, organic or organic-aqueous solutions of their salts to the zeolite by impregnating the zeolite with the salt solution. Supercritical $CO_2$ can also serve as solvent. Examples of salts are $Ru(NH_3)_6Cl_3$ as Ru salt and $(NH_4)_6Mo_7O_{24}$ as Mo salt. If the zeolite is to be doped with more than one metal, these can be applied successively as a solution of the respective salt or a number of them can be applied together in a solution comprising the desired metal salts. The wet-chemical treatments are followed by drying at about 100° C. under reduced pressure and then calcination at from about 400 to 600° C.

The metals can also be applied dry chemically to the zeolite, for example by depositing a metal compound which is gaseous at elevated temperatures from the gas phase onto the zeolite. This variant can be carried out using, for example, the carbonyl compounds of various transition metals which can be sublimed under reduced pressure. For example, Mo can in this way be deposited as $Mo(CO)_6$ onto the zeolite from the gas phase.

The above-described wet-chemical and dry-chemical processes for applying the metals to the zeolite can also be used in combination.

These zeolites, which may, if appropriate, comprise at least one of the abovementioned metals, can be processed by processes known to those skilled in the art to form shaped bodies. Shaping processes which may be mentioned are, for example, spraying of a suspension comprising the zeolites, tableting, pressing in the moist or dry state, extrusion or further processes known to those skilled in the art. At least two of these processes can also be combined. Thus, it is possible, for example, firstly to spray a suspension comprising the zeolite, for example in a spray drying process or a spray granulation process, and to subject the resulting sprayed material, if appropriate after at least one washing step and/or at least one drying and/or calcination step, to further shaping, for example extrusion. In the shaping process, it is possible to use auxiliaries such as pore formers, pasting agents, binders or other additives known to those skilled in the art. As possible binders, mention may be made of, for example, metal oxides such as $SiO_2$, $Al_2O_3$, $TiO_2$, $ZrO_2$ or MgO or clays or mixtures of two or more of these compounds. It is also possible to use precursors of these binders, with the binders mentioned being formed from these precursors during the course of the production process. Examples of such binder precursors are, for instance, tetraalkoxysilanes, tetraalkoxy titanates, tetraalkoxy zirconates or mixtures of two or more of these precursors. Possible pasting agents are compounds which lead to an improvement in the mixing, kneading and flow properties. For the purpose of the present invention, these are preferably organic, in particular hydrophilic, polymers such as cellulose, cellulose derivatives such as methylcellulose, starch such as potato starch, wallpaper paste, acrylates, polyacrylates, polymethyacrylates, polyvinyl alcohols, polyvinylpyrrolidone, polyisobutene, polytetrahydrofuran, polyglycol ethers, fatty acid compounds, wax emulsions, water or mixtures of two or more of these compounds. For the purposes of the present invention, pore formers are, for example, compounds which can be dispersed, suspended or emulsified in water or aqueous solvent mixtures, for example, polyalkylene oxides such as polyethylene oxides, polystyrene, polyacrylates, polymethacrylates, polyolefins, polyamides, polyesters, carbohydrates, cellulose, cellulose derivatives such as methylcellulose, sugar, natural fibers, pulp, graphite or mixtures of two or more of these compounds. Pore formers and/or pasting agents are preferably removed from the shaped body obtained after shaping by means of at least one suitable drying and/or calcination step.

The geometries of the catalysts obtained according to the invention can be, for example, spherical (hollow or solid), cylindrical (hollow or solid), ring-shaped, saddle-shaped, star-shaped, honeycomb-shaped or tablet-shaped. Furthermore, extrudates having the shape of, for example, rods, trilobes, quatrolobes, stars or hollow cylinders are possible. The catalyst can also be present as powder. Solid or hollow microspheres as can be obtained, for example, from the abovementioned spraying processes are likewise conceivable.

In a further embodiment of the invention, the shaped bodies can firstly be produced from the zeolite and the desired metals can subsequently be applied to the shaped bodies by the above-described methods.

In the process of the invention, it is possible to use one catalyst but it is also possible to use two or more different catalysts. The different catalysts can be present side-by-side, as mixtures or in layers in a reaction zone or in two or more successive reaction zones. The reaction zones can be located in one reactor or in a plurality of reactors.

In a preferred embodiment of the invention, the catalyst comprises from 0.2 to 10% by weight of Mo, preferably from 0.4 to 8% by weight, particularly preferably from 0.5 to 6% by weight, of Mo, and from 0.02 to 6% by weight of Ru, preferably from 0.04 to 5, particularly preferably from 0.05 to 4, % by weight of Ru.

Loss of metals used for doping the catalyst can occur during the course of the reaction, so that their concentration in or on the catalyst no longer corresponds to the desired concentration. To compensate for this loss of metals used for doping of the catalyst, the metals can be reapplied in the form of their carbonyls to the catalyst.

According to the invention, the reaction of the gas stream A comprising $C_1$-$C_6$-alkane and $N_2$ can in principle be carried out in all types of reactor known from the prior art which are suitable for solid-catalyzed gas-phase reactions.

Suitable reactor forms for use in the process of the invention are, for example, tube reactors or shell-and-tube reactors, in which the catalysts can more preferably be used as fixed-bed catalysts. Here, the catalyst is present as a fixed bed in a reaction tube or in a bundle of reaction tubes. Both the downflow mode of operation and the upflow mode of operation are possible as process variants. The internal diameters of the tubes can vary over a wide range, i.e. they can be in a range commencing at microns up to meters. Customary preferred industrial reaction tube internal diameters are from about 2 to 5 cm. However, smaller reaction tube internal diameters can also be used, for example in minireactors and microreactors. In a further embodiment, the tube internal diameters are in the range from 0.5 to 20 mm.

A typical shell-and-tube reactor comprises from about 2 to 30 000 reaction tubes.

The integrated preparation of ammonia and aromatics can also be carried out in a fluidized-bed or moving-bed reactor. A tray reactor is likewise suitable. This comprises one or more successive catalyst beds. The number of catalyst beds can be from 1 to 20, advantageously from 1 to 6, preferably from 1 to 4 and in particular from 1 to 3. The reaction gas preferably flows radially or axially through the catalyst beds. In general, such a tray reactor is operated using a fixed bed of catalyst. In the simplest case, the fixed beds of catalysts are arranged axially or in the annual gaps of concentric cylindrical meshes in a shaft furnace reactor. A shaft furnace reactor corresponds to a tray reactor having only one tray. The dehydrogenative aromatization in step 3) is preferably carried out in a shell-and-tube reactor or fluidized-bed reactor.

According to the invention, the reactor can comprise one reactor bed, but it can also be advantageous to operate a plurality of reactor beds in parallel, with one or more of these generally being in the state of regeneration or reactivation.

Before the reaction, the catalyst can be activated by heating to temperatures of from 350 to 450° C. in an inert gas atmosphere, for example under He or Ar.

Activation can also be effected by means of a methane-comprising gas stream or a $C_2$-$C_4$-alkane, for example ethane, propane, butane or a mixture of these; preference is given to using butane. The activation is carried out at a temperature of from 350 to 650° C., preferably from 400 to 550° C., and a pressure of from 0.5 to 5 bar, preferably from 0.5 to 2 bar. The GHSV (gas hourly space velocity) in the activation is usually from 100 to 4000 $h^{-1}$, preferably from 500 to 2000 $h^{-1}$.

It is also possible to carry out activation by means of the hydrocarbons having at least two carbon atoms which are comprised in the gas stream A. The activation is carried out at a temperature of from 250 to 650° C., preferably from 350 to 550° C., and a pressure of from 0.5 to 5 bar, preferably from 0.5 to 2 bar. The GHSV (gas hourly space velocity) in the activation is usually from 100 to 4000 $h^{-1}$, preferably from 500 to 2000 $h^{-1}$.

In a further embodiment, it is also possible to introduce additional hydrogen.

Of course, the catalyst used can be regenerated by customary methods known to those skilled in the art when its activity decreases. Mention may here be made of, in particular, treatment with an oxygen-comprising mixture such as air, enriched air or pure oxygen, in which the oxygen-comprising mixture is passed over the catalyst instead of the gas stream A. However, it is also possible, for example, to regenerate the catalyst by means of hydrogen. This can be effected by, for example, adding a hydrogen stream to the gas stream A. The ratio of hydrogen stream to gas stream A is usually in the range from 1:1000 to 2:1, preferably from 1:500 to 1:5.

According to the invention, the process for the integrated preparation of aromatics and ammonia is carried out over the abovementioned catalysts at temperatures of from 400 to 1000° C., preferably from 450 to 900° C., particularly preferably from 500 to 800° C., in particular from 550 to 750° C., at a pressure of from 0.5 to 100 bar, preferably from 1 to 50 bar, particularly preferably from 1 to 30 bar, in particular from 1 to 10 bar. The reaction is usually carried out at a GHSV (gas hourly space velocity) of from 100 to 10 000 $h^{-1}$, preferably from 200 to 6000 $h^{-1}$.

The product gas stream obtained after the reaction according to the invention comprises the aromatics formed in the aromatization reaction, e.g. benzene, toluene, xylene and naphthalene, by-products which may occur in the aromatization reaction, e.g. ethylene and acetylene, and also ammonia and unreacted hydrogen formed in the aromatization reaction. Further constituents of the product gas stream are unreacted starting materials, i.e. $C_1$-$C_6$-aliphatics and nitrogen, and also the impurities comprised therein.

In an embodiment of the invention, the aromatics are firstly separated off from the gas stream obtained after the reaction. The aromatics are separated off by condensation or fractional condensation. Thus, the mixture can be cooled to from −30° C. to 80° C., preferably to from 0° C. to 70° C., particularly preferably to from 30° C. to 60° C. The aromatic hydrocarbons condense here while the unreacted $C_1$-$C_6$-aliphatics, the nitrogen, the ammonia formed and further by-products formed in the reaction and possibly impurities previously comprised in the gas stream A are present in gaseous form and can thus be separated off by customary methods. The product gas stream can also be compressed before or after cooling and, if appropriate, be cooled further. Compression is preferably carried out to a pressure level of from 1 to 100 bar, more preferably from 1 to 75 bar and even more preferably from 5 to 15 bar. To achieve substantial condensation of a particular compound, an appropriate temperature is set.

Ammonia comprised in the product gas stream which has been freed or aromatics can be condensed and separated off by further cooling of the stream. At atmospheric pressure, this is preferably carried out at temperatures below −33° C. As an alternative, the ammonia can also be separated off by passing the gas stream through water.

The ammonia can also be removed by reversible adsorption and desorption (thermal or pressure swing adsorption) from the product gas stream which has been freed of aromatics.

In a further embodiment of the invention, the hydrogen which has not been consumed in the ammonia synthesis can be removed from the gas stream by customary methods known to those skilled in the art, for example by passing the gas stream along a membrane which is selectively permeable to molecular hydrogen or by reversibly adsorbing (thermal or pressure swing adsorption) the other components comprised in the gas stream and subsequently desorbing them again.

The gas stream which has been freed of aromatics, ammonia and, if appropriate, hydrogen can be recirculated in part or in its entirety to the reaction zone. If appropriate, the $C_1$-$C_6$-aliphatics can also be separated off from the gas stream and recirculated to the reaction zone.

The invention is illustrated below by means of examples.

EXAMPLES

The reactions in examples 2, 3 and 4 are carried out in a commercially available TPR-TPO-TPD apparatus (AutoChemII2920, from Micromeritics, combined with an OmniStar and QMS200 mass spectrometer, from Pfeiffer Vacuum). The apparatus comprised a fused silica reactor having a length of 205 mm and an internal diameter of 9 mm.

Example 1

Production of the Catalyst, According to the Invention 500 g of a zeolite powder having an MFI structure (PZ 2/25; from Zeochem, Uetikon, Switzerland) are treated in a three-neck glass flask with 5 kg of a solution of 500 g of ammonia nitrate in 4500 g of deionized water at 80° C. for 2 hours while stirring. The solid is then filtered off, washed with water until neutral and dried overnight at 120° C. in air. The weight of solid obtained is 592 g.

20 g of this solid are treated in a smaller stirred flask with a solution of 0.092 g of hexammineruthenium(III) chloride in 1000 g of deionized water at room temperature for 50 hours. The suspension formed is filtered, the solid is washed until neutral and dried as described above. The weight of solid obtained is 19.5 g.

In a rotary tube, 17 of this solid from the ruthenium treatment are treated at 400° C. in a stream of helium for 2 hours (heating rate: 4° C./min). After cooling, the gray powder is transferred in a nitrogen atmosphere to a Schlenk tube; the weight of solid obtained is 14 g.

2.5 g of molybdenum hexacarbonyl are placed in a second Schlenk tube and purified by resublimation at 150° C. under reduced pressure a total of 3 times, with the purified molybdenum hexacarbonyl depositing on the walls in the upper region of the Schlenk tube.

A portion of fused silica wool is placed in the Schlenk tube comprising the prepurified molybdenum hexacarbonyl about 2 cm above the bed of the carbonyl powder and the ruthenium-treated zeolite powder is placed on top of the wall. The Schlenk tube is subsequently evacuated to a pressure of from 8 to 12 mbar at room temperature for 1 hour, and the vessel is subsequently placed in an oil bath and heated to 130° C. After the molybdenum hexacarbonyl at the bottom of the vessel has vaporized completely, the glass vessel is cooled and maintained at 80° C. for a further 24 hours. It is then cooled to room temperature and inert gas (nitrogen) is admitted.

Example 2

Production of Ammonia from Nitrogen and Hydrogen, Not According to the Invention The apparatus including reactor is subsequently flushed under atmospheric pressure with a flow of 30 ml/min of helium (from Praxair, purity 6.0), then heated to 400° C. at a heating rate of 10° C./min and maintained at this temperature for 120 minutes. The reactor is subsequently heated to 450° C. at a heating rate of 10° C./min under a flow of 25 ml/min of helium and maintained under these conditions for 30 minutes.

51 mg of catalyst from example 1 are fixed in the reactor as a micro fixed bed with a plug of glass wall to hold the catalyst.

The helium flow is changed over to a flow of 25 ml/min of a mixture of 25% by volume of nitrogen (from Air Liquide, purity: 4.6) and 75% by volume of hydrogen (from Air Liquide, purity: 5.0). The reactor is heated to 550° C. at a rate of 2° C./min and maintained at this temperature for 1 hour, then heated further to 650° C. at 2° C./min and maintained at this temperature for 60 minutes.

The gas at the outlet of the reactor is collected in a cold trap at −196° C. The output collected in the cold trap is evaluated by two different test persons who both observe a pungent odor of ammonia.

Example 3

Production of Aromatics and Ammonia from Methane and Nitrogen, According to the Invention The apparatus including reactor is subsequently flushed under atmospheric pressure with a flow of 30 ml/min of helium (from Praxair, purity 6.0), then heated to 400° C. at a heating rate of 10° C./min, maintained under these conditions for 120 minutes, then heated to a reactor temperature of 450° C. at a heating rate of 10° C./min at a helium flow of 25 ml/min and maintained under these conditions for 30 minutes. 198 mg of catalyst (from example 1) are fixed in the fused silica reactor as a micro fixed bed with a plug of glass wool to hold the catalyst.

The reactor temperature is increased from 450° C. to 500° C. at a heating rate of 10° C./min and, after a hold time of about 15 minutes, increased further at a heating rate of 30° C./min to a maximum of 650° C. and this temperature is maintained for 30 minutes. At this temperature, the gas flow is changed to a flow of 25 ml/min of a gas mixture of 58% by volume of methane (from Air Liquide, purity: 2.5) and 42% by volume of nitrogen. The gas at the outlet of the reactor is collected in a cold trap at −196° C. for a number of hours, taken up in 2.6 g of ethanol (AR) and analyzed. The ammonia content of the collected output is determined by ion chromatography and is 10 mg/kg. The benzene content determined by gas chromatography is 30 mg/kg. The catalyst removed from the reactor is dark black and has a weight of 259 mg.

The invention claimed is:

1. A process for the integrated preparation of aromatics and ammonia by reaction of a gas stream A comprising at least one $C_1$-$C_6$-aliphatic and nitrogen in the presence of at least one catalyst, wherein the $C_1$-$C_6$-aliphatics are converted non-oxidatively into aromatics in one reaction and the hydrogen liberated in this reaction is reacted with nitrogen to form ammonia in a further reaction.

2. The process according to claim 1, wherein the at least one catalyst comprises zeolite.

3. The process according to claim 1, wherein the at least one catalyst is doped with one or more transition metals.

4. The process according to claim 1, wherein the at least one catalyst is doped with one or more transition metals selected from the group consisting of Mn, Mo, Pd, Pt, Ru, Cu, Co, Fe, Re, W and Zn.

5. The process according to claim 1, wherein the at least one catalyst comprises from 0.2 to 10% by weight of Mo and from 0.02 to 6% by weight of Ru.

6. The process according to claim 1, wherein the at least one catalyst comprises zeolite of the MFI type.

7. The process according to claim 1, wherein the $C_1$-$C_6$ aliphatic is natural gas.

8. The process according to claim 1, wherein the ratio of $C_1$-$C_6$ aliphatic to $N_2$ based on the volumes in the gas stream A is from 1:1 to 20:1.

9. The process according to claim 1, wherein the reaction is carried out at temperatures of from 400° C. to 1000° C. and pressures of from 0.5 bar to 100 bar.

10. The process according to claim 1, wherein the reaction is carried out at gas space velocities of from 100 to 10 000 $h^{-1}$.

11. The process according to claim 1, wherein the reaction is carried out in a fixed-bed or fluidized-bed reactor.

12. The process according to claim 1, wherein the $C_1$-$C_6$ aliphatic comprises natural gas.

* * * * *